United States Patent [19]

Karol

[11] Patent Number: 4,904,403

[45] Date of Patent: Feb. 27, 1990

[54] POLYALKYLATED 1,3,4-THIADIAZOLES AND LUBRICATING COMPOSITIONS CONTAINING SAME

[75] Inventor: Thomas J. Karol, Norwalk, Conn.

[73] Assignee: R. T. Vanderbilt Company, Inc., Norwalk, Conn.

[21] Appl. No.: 364,415

[22] Filed: Jun. 12, 1989

[51] Int. Cl.$^4$ .............................................. C10M 1/38
[52] U.S. Cl. ................................ 252/47.5; 252/47; 252/406; 548/142
[58] Field of Search ................... 252/47, 47.5; 548/142

[56] References Cited

U.S. PATENT DOCUMENTS

| | | | |
|---|---|---|---|
| 2,719,125 | 9/1955 | Roberts | 252/46.7 |
| 2,719,126 | 9/1955 | Fields et al. | 252/47 |
| 2,736,729 | 2/1956 | Krzikalla et al. | 260/302 |
| 2,850,453 | 9/1958 | Fields | 252/32.7 |
| 3,980,573 | 9/1976 | Okorodudu | 252/46.7 |
| 4,301,019 | 11/1981 | Horodysky | 252/47.5 |
| 4,306,988 | 12/1981 | Rothgery | 252/150 |
| 4,410,703 | 10/1983 | Okorodudu | 548/142 |
| 4,790,948 | 12/1988 | Liu et al. | 252/47.5 |

FOREIGN PATENT DOCUMENTS

| | | | |
|---|---|---|---|
| 966842 | 4/1975 | Canada | 260/308.3 |
| 1048994 | 2/1979 | Canada | 252/47.5 |
| B28560 | 10/1955 | Fed. Rep. of Germany | 252/47.5 |

*Primary Examiner*—William R. Dixon, Jr.
*Assistant Examiner*—Miriam Sohn
*Attorney, Agent, or Firm*—Rasma B. Balodis

[57] ABSTRACT

Disclosed are novel compounds derived from 2,5-dimercapto-1,3,4-thiadiazole and one or two moles of polyolefin having 5 to 400 carbon atoms. Furthermore, the 5-position of the 2-mercapto-1,3,4-thiadiazole may be substituted by alkylthio, 2-hydroxyalkylthio, amino or hydroxy group. The compounds are effective dispersants, antiwear agents and antioxidants when incorporated into lubricating compositions.

4 Claims, No Drawings

POLYALKYLATED 1,3,4-THIADIAZOLES AND LUBRICATING COMPOSITIONS CONTAINING SAME

BACKGROUND OF THE INVENTION

The present invention concerns novel derivatives of thiadiazole compounds. More particularly, the novel thiadiazoles are derived from a polyolefin and 1,3,4-thiadiazole compound. The invention further concerns improved lubricating compositions containing said thiadiazole derivatives.

During normal operation of internal combustion engines, oil-insoluble sludge forms in the crankcase and oil passages of a gasoline or diesel engine. Sludge affects the ability of the lubricating oil to effectively lubricate the engine parts and, by entrapment of water, contributes to rust formation in the engine.

To prevent sludge formation on the engine, dispersants or detergents are added to the lubricating formulation. The additives maintain sludge particles suspended in the oil and thus minimize deposits on the engine surfaces and on the oil filter.

Known detergents or dispersants are either metal salts or of the ashless type. Due to environmental considerations, ashless dispersants are preferred. For economical reasons, it is also preferred that the additive possesses other functional properties for improving the lubricating properties of the oil.

It has been surprisingly discovered that certain polyalkylated 1,3,4-thiadiazoles possess dispersant as well as antiwear and antioxidant properties.

In prior art, lower chain alkyl derivatives of 2,5-disulfinyl-1,3,4-thiadiazoles have been disclosed as surfactants in U.S. Pat. No. 4,432,847.

SUMMARY OF THE INVENTION

In accordance with the invention, there are provided novel polyalkylated 1,3,4-thiadiazole compounds characterized by the structural formula

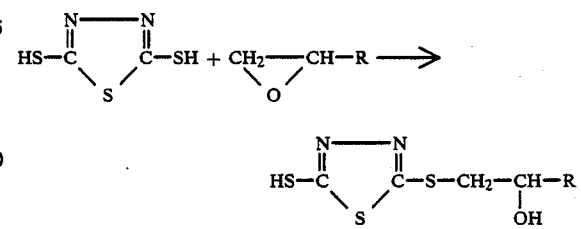

wherein $R^1$ represents hydroxy, amino, mercapto, alkylthio, 2-hydroxyalkylthio or $R^2S$-group and $R^2$ represents a polyolefin residue and is characterized by the formulae

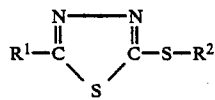

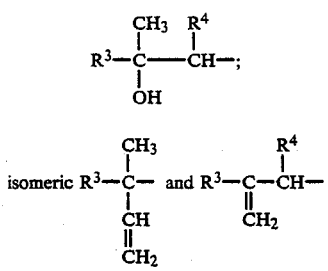

wherein $R^3$ is an alkyl group having 50 to 400 carbon atoms and $R^4$ is hydrogen or methyl group.

Another aspect of the invention concerns improved oil-based lubricating compositions comprising a major amount of base oil and an amount sufficient to impart dispersant, antiwear and antioxidant characteristics to said composition, of a polyalkylated 1,3,4-thiadiazole characterized by formula I.

DESCRIPTION OF SPECIFIC EMBODIMENTS

The novel compounds of the invention may be prepared by reacting 2,5-dimercapto-1,3,4-thiadiazole with one or two molar equivalents of a polyolefin having an epoxidized or chlorinated end unit.

The general reaction scheme is illustrated by the following equation wherein R represents a polyolefin residue.

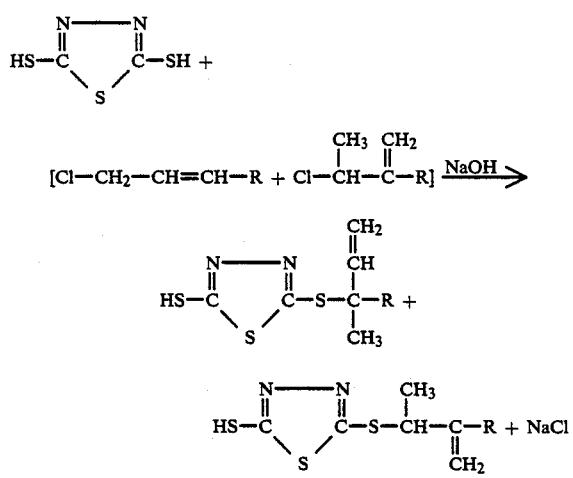

Preferably, the reaction is conducted in the presence of an inert solvent such as alcohols, toluene and acetone. The reaction temperature will depend upon the specific reactants and solvent media employed. Typically, reaction temperatures range from about $-5°$ C. to $60°$ C.

The chlorinated polymer starting material is typically an isomeric mixture. Therefore, a chlorine displacement causing a bond shift will occur with the formation of two isomers.

The amino derivatives of the invention may be prepared from commercially available 2-amino-5-mercapto-1,3,4-thiadiazole precursor by similar reaction schemes. The hydroxy derivatives may be prepared by reacting the mercapto group with propylene oxide followed by sodium hydroxide treatment. Some hydrocarbon substitution may occur on the nitrogen and oxygen atom. Furthermore, in all described monohydrocarbyl substitution reactions some dihydrocarbyl substituted derivatives may form as byproducts.

The polyolefin starting material is a hydrocarbon polymer with an epoxide or chlorine functionality at one end. The polymeric chain contains at least 50 carbon atoms and may range to about 400 carbon atoms.

Typically, the molecular weight of the polyolefin ranges from 100 to 5000 and higher. The polymers are prepared by copolymerizing olefins as for example ethylene, propylene and butylene. Preferred are polymers containing tertiary alkyl units having about 50 to 200 carbon atoms. Especially useful are polymers of alpha-olefins as for example isoprene, isobutene, 2-methyl-1-heptene, and 2-methyl-5-propylhexene.

Activated polyolefins are available commercially. For, example, activated polyisobutenes with epoxide functionality are marketed under the tradename ACTIPOL TM by Amoco Chemical Company. Alternately, commercial polyolefins may be epoxidized by known methods.

The thiadiazole derivatives of the invention are useful as lubricating additives. The compounds possess multifunctional properties. In addition to being capable of acting as dispersants, they also perform antiwear and antioxidant functions.

The lubricating compositions contemplated herein include lubricating oils and lubricating greases containing a major amount of base oil. The base oil may be selected from oils derived from petroleum hydrocarbon and synthetic sources. The hydrocarbon base oil may be selected from naphthenic, aromatic, and paraffinic mineral oils. The synthetic oils may be selected from, among others, alkylene polymers, polysiloxanes, carboxylic acid esters and polyglycol ethers.

The amount of the thiadiazole additive required to be effective for imparting dispersing, antiwear and antioxidant characteristics in lubricating compositions may range from about 0.01 to 10 percent of the lubricating composition. The preferred range is about 0.1 to 5.0 percent of the additive of the total lubricating composition.

The lubricating compositions may contain the necessary ingredients to prepare the composition as for example emulsifiers and viscosity improvers. Greases may be prepared by adding thickeners as for example salts and complexes of fatty acids, polyurea compounds, clays and quaternary ammonium bentonite. Depending on the intended use of the lubricant, other functional additives may be added to enhance a particular property of the lubricant. The lubricating compositions may further contain extreme pressure agents, metal passivators, rust inhibitors and other known antioxidants and antiwear agents.

The following examples are given for the purpose of further illustrating the invention. All percentages and parts are based on weight unless otherwise indicated.

EXAMPLE 1

2,5-Dimercapto-1,3,4-thiadiazole (hereinafter DMTD) (159 g, 1.06 mol), methylene chloride (1000 ml), and acetone (1000 ml) were charged to a reaction vessel. Epoxidized polyisobutylene with an average molecular weight of 973 (1031.4 g, 1.06 mol) was added with stirring. The reaction mixture was allowed to react overnight with stirring and for 24 hours thereafter without stirring. The solvent was stripped off on a rotary evaporator under a reduced pressure. Pentane (500 ml) was added to precipitate unreacted DMTD. The filtered product contained 67–78 percent active ingredient, i.e. DMTD reaction product.

EXAMPLE 2

The adduct of Example 1 (218 g) was further reacted with 1,2-epoxybutane (12 g) in the solvent media of isopropanol (150 ml) and hexane (150 ml) by refluxing for one hour. The product, 2-hydroxybutyl derivative of the DMTD-epoxidized polysobutylene adduct was recovered by stripping under reduced pressure on a rotary evaporator.

EXAMPLE 3

The adduct of Example 1 (78 percent active ingredient, 250.25 g, 0.174 mol), toluene (200 ml), isopropanol (50 ml) and propylene oxide (15 g, 0.24 mol) were charged to a reaction vessel fitted with a reflux condenser and stirrer and brought to reflux with stirring. The reaction mixture was refluxed for one hour and then vacuum-stripped to remove propylene oxide. Toluene (100 ml), water (25 ml) and 50% aqueous sodium hydroxide solution were charged to the reaction vessel with stirring and warmed at 50°–60° C. for 0.5 hour. Sulfuric acid (25 ml) in water (100 ml) was slowly added with stirring and the reaction was washed with water. Then water was left in contact with the organic layer for 24 hours. The organic layer was isolated and stripped to recover the hydroxy analog.

EXAMPLE 4

Epoxide polyisobutylene with average molecular weight of 365 (373 g, 1.02 mol) and isopropanol (500 ml) were charged into a reaction vessel and DMTD (125 g, 0.813 mol) was added with stirring. After stirring the reaction mixture for 48 hours at room temperature, isopropanol solvent was stripped off under reduced pressure on a rotary evaporator and the product was diluted with hexane (250 ml) and filtered to remove unreacted DMTD. Hexane was stripped off as the previous solvent. The yield was 80.3 percent of active product.

EXAMPLE 5

Polyisobutylene with average molecular weight of 950 and methylene chloride (250 ml) were charged into a reaction flask fitted with a gas inlet and outlet. The outlet was fitted with a caustic trap and the inlet was fitted with a vacuum flask to prevent liquid flow-back. Chlorine (41.6 g, 0.59 mol) was bubbled into the reaction with stirring. Hydrogen chloride evolved as chlorine was consumed. After stirring for 0.5 hours, the product was transferred to separatory funnel, diluted with hexane (200 ml), washed with water (300 ml), 1M sodium bicarbonate (300 ml) and water (300 ml). The product was dried over magnesium sulfate, filtered and the diluent solvent removed by rotary evaporation under a reduced pressure.

The chlorinated polyisobutylene product (141.7 g) was diluted with tetrahydrofuran (400 ml) and reacted with 32.8 percent of aqueous solution of monosodium salt of DMTD. The reaction was refluxed with stirring for 6 hours. The solvents were stripped off under vacuum until the reaction temperature reached 100° C. After release of vacuum and cooling, tetrahydrofuran (300 ml) was charged. The reaction was again refluxed for 4 hours. Solvent was stripped off as above. The product was extracted with hexane, washed with water, filtered, and dried over magnesium sulfate. Solvent was stripped off by rotary evaporation under nitrogen to afford the product.

EXAMPLE 6

Polyisobutylene with average molecular weight of 450 (500 g, 1.11 mol) was epoxidized with a solution consisting of acetic acid (30 g), 70 percent of methanesulfonic acid (7.6 g) and 70 percent hydrogen peroxide (100 g) on water bath at 45° to 50° C. for 5.5 hours. The product was separated in a separatory funnel, diluted with hexane (250 ml) and washed with water (4×400 ml). The product had a 77 percent active epoxide and the yield was 527.5 g.

EXAMPLE 7

The intermediate of Example 4 (360 g, 0.59 mol), acetone (300 ml) and DMTD (44.6 g, 0.297 mol) were charged to the reactor and stirred at room temperature overnight. The reaction was then heated to reflux at about 60° C. for 3 hours. The acetone was distilled off until the reaction temperature reached 100° C. The product was then stripped of solvent under reduced pressure on a rotary evaporator.

EXAMPLE 8

Dispersion Test

Dispersancy of lubricating compositions containing the compounds of the invention was measured by the Bench Sequence V Test. Test samples were prepared by mixing nonformulated 150 SN base oil (manufactured by Exxon Co.), synthetic blow-by and the test formulation. The synthetic blow-by was prepared from fuel bottoms (150° C. distillate fractions and heavier) by nitrooxidation with 25,000 ppm nitrogen oxide in air mixture. Commercial fully formulated oil was used as positive reference standard. The test formulation of the invention was prepared by adding as dispersant 2.5 percent active product of Example 1 to a prototype reference oil containing no other dispersants. The test samples were heated for four hours at 138° C. in a mechanical convection oven. After cooling, turbidity was measured by using a Lumetron Photoelectric Colorimeter. Dispersancy is inversely related to turbidity. Satisfactory dispersancy is indicated by low turbidity, that is, below 60 turbidity units expressed as lumens. The test results are compiled in Table I.

TABLE I

| Dispersion Test | | | |
|---|---|---|---|
| | Composition, ml | | |
| Composition | 1 | 2 | 3 |
| 150 SN Base Oil | 4.12 | 4.12 | 4.12 |
| Synthetic blow-by | 2.2 | 2.2 | 2.2 |
| Reference oil | — | 0.38 | — |
| Test formulation containing product of Example 1 | — | — | 0.38 |
| Turbidity, average lumens | 187.5 | 31 | 30 |

EXAMPLE 9

Shell Four-Ball Wear Test

The test was conducted essentially according to the method described in ASTM D-2266 procedure. Four highly polished steel balls 12.5 mm in diameter were placed in a test cup and submerged in the test sample. The test oil was Sunvis TM 21 manufactured by Sun Oil Company. The test was carried out at a rotation speed of 1800 rpm under a load of 40 kg at 93° C. for 60 minutes. The diameter of wear scar produced by sample by containing additive of the invention was measured. The epoxidized polyisobutylene having 70 carbon atoms was 74% active and was prepared essentially by the method described in Example 1. The data indicate that the additive of the invention has good antiwear properties even when present at the relatively low quantity of 0.1 percent. Sunvis 21 alone typically affords a scar of 1.75-1.85.

TABLE II

| | Four-Ball Wear Test | | |
|---|---|---|---|
| Sample | Active Ingredient | Percent | Scar Diameter, mm |
| 4 | None | — | 1.75-1.85 |
| 5 | Product Example 1 | 0.1 | 0.81 |

EXAMPLE 10

Thin Film Oxygen Uptake Test

The test was conducted essentially according to the method described by Chia-Soon Ku et al, *J. Am. Soc. Lubricating Eng.*, 40, 2 75-83, 1984. The oxidation induction time of the lubricant was measured under conditions which simulate the high temperature oxidation processes in automotive engines by a modified rotary bomb oxidation test method ASTM D-2272. The test was conducted with 1.5 gram samples of Sunvis TM 21 oil manufactured by Sun Oil Company. Epoxidized polyisobutylene having 70 carbon atoms and 74% activity was prepared by the method described in Example 1 and added to the oil in the amount indicated for sample 7 in Table III. The test was conducted at 160° C. and initial oxygen pressure of 620.6 kPa (90 psi). A "pass" oil has a high induction time, while a "fail" oil has a low time. The additive of the invention has good antioxidant properties as indicated by the data compiled in Table III.

TABLE III

| Thin Film Oxygen Uptake Test | | |
|---|---|---|
| Sample | Additive Percent | Average Induction Time, Min. |
| 6 | None | 90.0 |
| 7 | 2.5 | 191.0 |

The above embodiments have shown various aspects of the present invention. Other variations will be evident to those skilled in the art and such modifications are intended to be within the scope of the invention as defined by the appended claims.

What is claimed is:

1. A compound having the structural formula

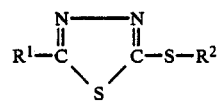

wherein $R^1$ represents hydroxy, amino, mercapto, alkylthio, 2-hydroxyalkylthio or $R^2S$-group and $R^2$ represents a polyolefin residue and is characterised by the formulae

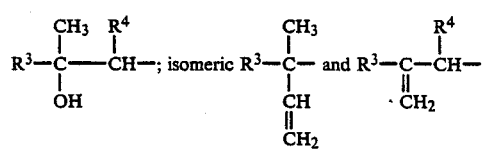

wherein $R^3$ is an alkyl group having 50 to 400 carbon atoms and $R^4$ is hydrogen or methyl group.

2. A composition comprising a major amount of oil of lubricating viscosity selected from the group consisting of petroleum hydrocarbon oil and synthetic oil and from about 0.1 to 10 percent by weight of a compound having the structural formula

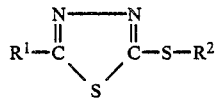

wherein $R^1$ represents hydroxy, amino, mercapto, alkylthio, 2-hydroxyalkylthio or $R^2S$-group and $R^2$ represents a polyolefin residue and is characterized by the formulae

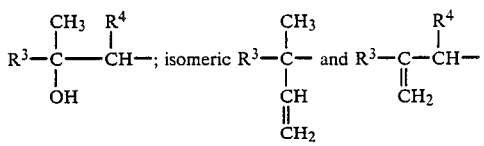

wherein $R^3$ is an alkyl group having 50 to 400 carbon atoms and $R^4$ is hydrogen or methyl group.

3. A compound according to claim 1 wherein the polyolefin residue is derived from epoxidized polyolefin having 50 to 200 carbon atoms.

4. A compound according to claim 1 wherein the polyolefin residue is derived from chlorinated polyolefin having 50 to 200 carbon atoms.

* * * * *